United States Patent
Wächtler et al.

[11] Patent Number: 5,811,029
[45] Date of Patent: Sep. 22, 1998

[54] BENZENE DERIVATIVES, AND A LIQUID-CRYSTALLINE MEDIUM

[75] Inventors: Andreas Wächtler, Griesheim; Reinhard Hittich, Modautal; Eike Poetsch, Mühltal; Herbert Plach, Darmstadt, all of Germany; David Coates, Merley, Great Britain; Ulrich Finkenzeller, Plankstadt, Germany; Thomas Geelhaar, Mainz, Germany; Volker Reiffenrath, Rossdorf, Germany; Bernhard Rieger, Münster-Altheim, Germany

[73] Assignee: Merck Patent Gesellschaft Mit Beschrankter Haftung, Germany

[21] Appl. No.: 387,438

[22] Filed: Feb. 13, 1995

Related U.S. Application Data

[62] Division of Ser. No. 957,051, Oct. 6, 1992, Pat. No. 5,389,295.

[30] Foreign Application Priority Data

| Aug. 12, 1989 | [DE] | Germany | 39 26 746.6 |
| Aug. 12, 1989 | [DE] | Germany | 39 26 749.0 |
| Aug. 31, 1989 | [DE] | Germany | 39 28 818.8 |
| Jan. 9, 1990 | [DE] | Germany | 40 00 392.2 |
| Jan. 22, 1990 | [DE] | Germany | 40 01 685.4 |
| Mar. 13, 1990 | [DE] | Germany | 40 07 864.7 |
| Mar. 28, 1990 | [DE] | Germany | 40 09 908.3 |

[51] Int. Cl.⁶ ............... C09K 19/30; C07C 255/00
[52] U.S. Cl. ............... 252/299.63; 252/299.66; 558/414; 558/423
[58] Field of Search ............... 252/299.63, 299.66; 558/423, 414

[56] References Cited

U.S. PATENT DOCUMENTS

| 4,468,340 | 8/1984 | Inoue et al. |
| 4,818,428 | 4/1989 | Scheuble et al. |
| 4,822,519 | 4/1989 | Saito et al. |
| 4,886,621 | 12/1989 | Sage et al. |
| 5,032,313 | 7/1991 | Goto et al. |
| 5,045,229 | 9/1991 | Bartmann et al. |
| 5,315,024 | 5/1994 | Takatsu et al. ............ 252/299.63 |
| 5,389,295 | 2/1995 | Wachtler ............ 252/299.63 |
| 5,616,284 | 4/1997 | Hittich et al. ............ 252/299.63 |

FOREIGN PATENT DOCUMENTS

| 3631611 | 4/1988 | Germany. |
| 1225147 | 10/1986 | Japan. |
| 8902884 | 4/1989 | WIPO. |

OTHER PUBLICATIONS

Abstract of JP 61–225147, (1986).

*Primary Examiner*—Philip Tucker
*Attorney, Agent, or Firm*—Millen, White, Zelano & Branigan, P.C.

[57] ABSTRACT

Benzene derivatives of the formula I

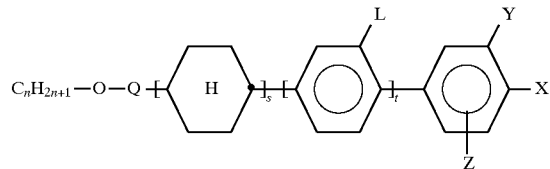

in which n is 1 to 7, Q is —CO— or —(CH$_2$)$_r$— where r is 1 to 5, s is 0, 1 or 2, t is 0 or 1, where s+t≧1, X is F, Cl, —CF$_3$, —CN, —OCF$_3$ or —OCHF$_2$, and Y, L and Z are each, independently of one another, H or F.

4 Claims, No Drawings

BENZENE DERIVATIVES, AND A LIQUID-CRYSTALLINE MEDIUM

This is a division, of the application Ser. No. 07/957,051 filed Oct. 6, 1992, now U.S. Pat. No. 5,389,295.

Benzene derivatives, and a liquid-crystalline medium The invention relates to novel benzene derivatives of the formula I

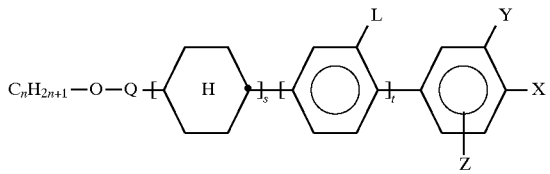

in which n is 1 to 7, Q is —CO or —$(CH_2)_r$— where r is 1 to 5, s is 0, 1 or 2, t is 0 or 1, where s+t$\geq$1, X is F, Cl, —$CF_3$, —CN, —$OCF_3$ or —$OCHF_2$ and Y, L and Z are each, independently of one another, H or F.

European Offenlegungsschrift 0,058,981 discloses liquid crystals which carry a radical of the formula —$CH_2$—O—$C_mH_{2m+1}$ (m=1 to 12). However, the compounds described therein do not carry any fluorine-containing radicals and are predominantly liquid crystals having more or less neutral dielectric anisotropy. The only dielectrically positive liquid crystal described is a compound of the formula

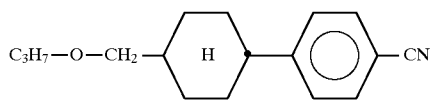

JP 57-108,056-A discloses liquid crystals of the formula

(n=1 to 9).

However, compounds of this type do not meet the high requirements regarding electrical resistance, as demanded, for example, for displays having an active matrix. In addition, compounds of this type have an extremely high temperature dependence of the threshold voltage and clear points which are unusually low for benzonitriles.

Like similar compounds, for example those disclosed in German Offenlegungsschriften 2,636,684 and 2,356,085, the compounds of the formula I are used as components of liquid-crystalline media, in particular for displays based on the principle of the twisted cell.

All the substances employed hitherto for this purpose have certain disadvantages, for example excessively high melting points, excessively low clear points, inadequate stability to heat, light or electrical fields, inadequate electrical resistance, in particular at high temperatures and/or under the action of UV radiation, unfavourable elastic properties for the particular application, and an excessive temperature dependence of the threshold voltage.

In particular in the case of displays of the supertwist type (STN) having twist angles of considerably more than 220° or in the case of displays having an active matrix, the materials employed hitherto have disadvantages.

The invention had the object of finding novel liquid-crystalline compounds which are suitable as components of liquid-crystalline media, in particular for nematic media having positive dielectric anisotropy, and which do not have the disadvantages of the known compounds, or only do so to a small extent. This object has been achieved by the provision of the novel compounds of the formula I.

It has been found that the compounds of the formula I are pre-eminently suitable as components of liquid-crystalline media. They can be used, in particular, to obtain liquid-crystalline media having broad nematic ranges, excellent nematogeneity down to low temperatures, excellent chemical stability, excellent elastic properties, a pronounced $\epsilon$ with a positive dielectric anisotropy, low temperature dependence of the threshold voltage and/or low optical anisotropy. The novel compounds also exhibit good solubility for other components of media of this type and a high positive dielectric anisotropy at the same time as favourable viscosity.

The compounds of the formula I facilitate both STN displays having a very steep electro-optical characteristic line and displays having an active matrix which have excellent long-term stability. Through a suitable choice of r and n, the threshold voltages can be considerably reduced in both types of display.

In the pure state, the compounds of the formula I are colourless and form liquid-crystalline mesophases in a temperature range which is favourably located for electro-optical use.

The invention thus relates to the compounds of the formula I and to the use of the compounds of the formula I as components of liquid-crystalline media, to liquid-crystalline media containing at least one compound of the formula I, and to electro-optical displays which contain media of this type.

Above and below, r, Q, n, s, t, L, X, Y and Z are as defined, unless expressly stated otherwise.

In the case where X is CN, preference is given to compounds where s=2 and t=0 or s=1 and t=1 (where L is H or preferably F) and/or n is 2 to 7 and/or r is 2 to 5.

In the compounds of the formula I, the alkyl groups $C_nH_{2n+1}$ are preferably straight-chain. Accordingly, $C_nH_{2n+1}$ is preferably methyl, ethyl, n-propyl, n-butyl, n-pentyl, n-hexyl or n-heptyl. n is preferably 1, 2, 3, 4 or 5, particularly preferably 1. r is preferably 2, 3, 4 or 5 particularly preferably 2 or 3. Furthermore, r is preferably 1, in particular when s+t$\geq$2.

Compounds of the formula I containing branched alkyl groups may occasionally be important due to better solubility in the customary liquid-crystalline base materials, but in particular as chiral dopes, if they are optically active. Branched groups of this type generally contain not more than one chain branch. Preferred branched alkyl radicals are isopropyl, 2-butyl (=1-methylpropyl), isobutyl (=2-methylpropyl), 2-methylbutyl, isopentyl (=3-methylbutyl), 2-methylpentyl, 3-methylpentyl or 2-heptyl (=1-methylhexyl). The radical

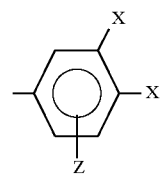

is preferably

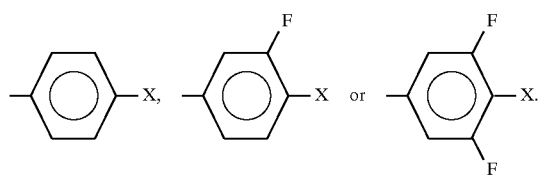

X is preferably F, Cl, —CF$_3$, —OCHF$_2$ or —OCF$_3$.
Q is preferably —(CH$_2$)$_r$—.

In addition, the compounds of the formula I are prepared by methods known per se, and described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for the reactions mentioned. Use may also be made here of variants which are known per se, but are not described here in greater detail.

If desired, the starting materials can also be formed in situ by not isolating them from the reaction mixture, but instead immediately reacting them further to form the compounds of the formula I.

Precursors which are suitable for the synthesis of the compounds according to the invention can be obtained, for example, by the following synthesis scheme:

Scheme 1a:

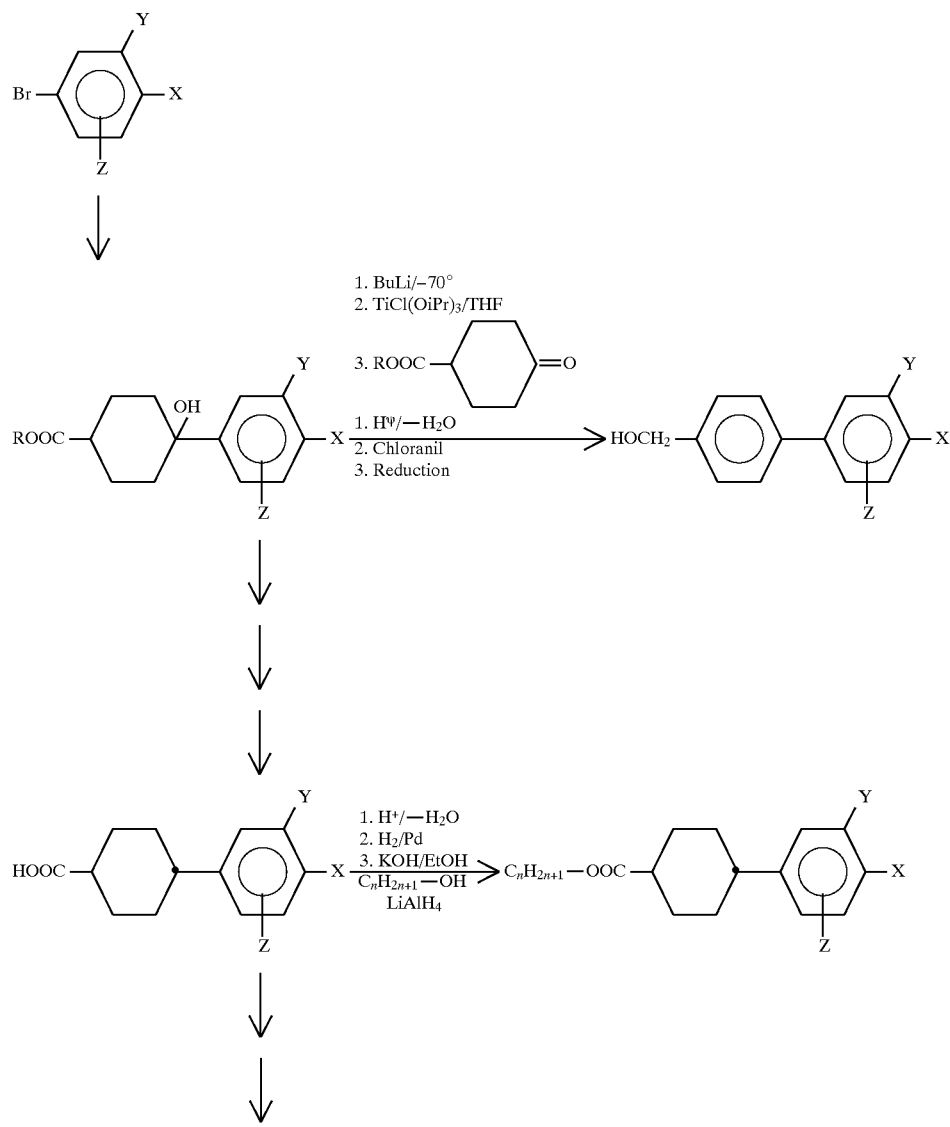

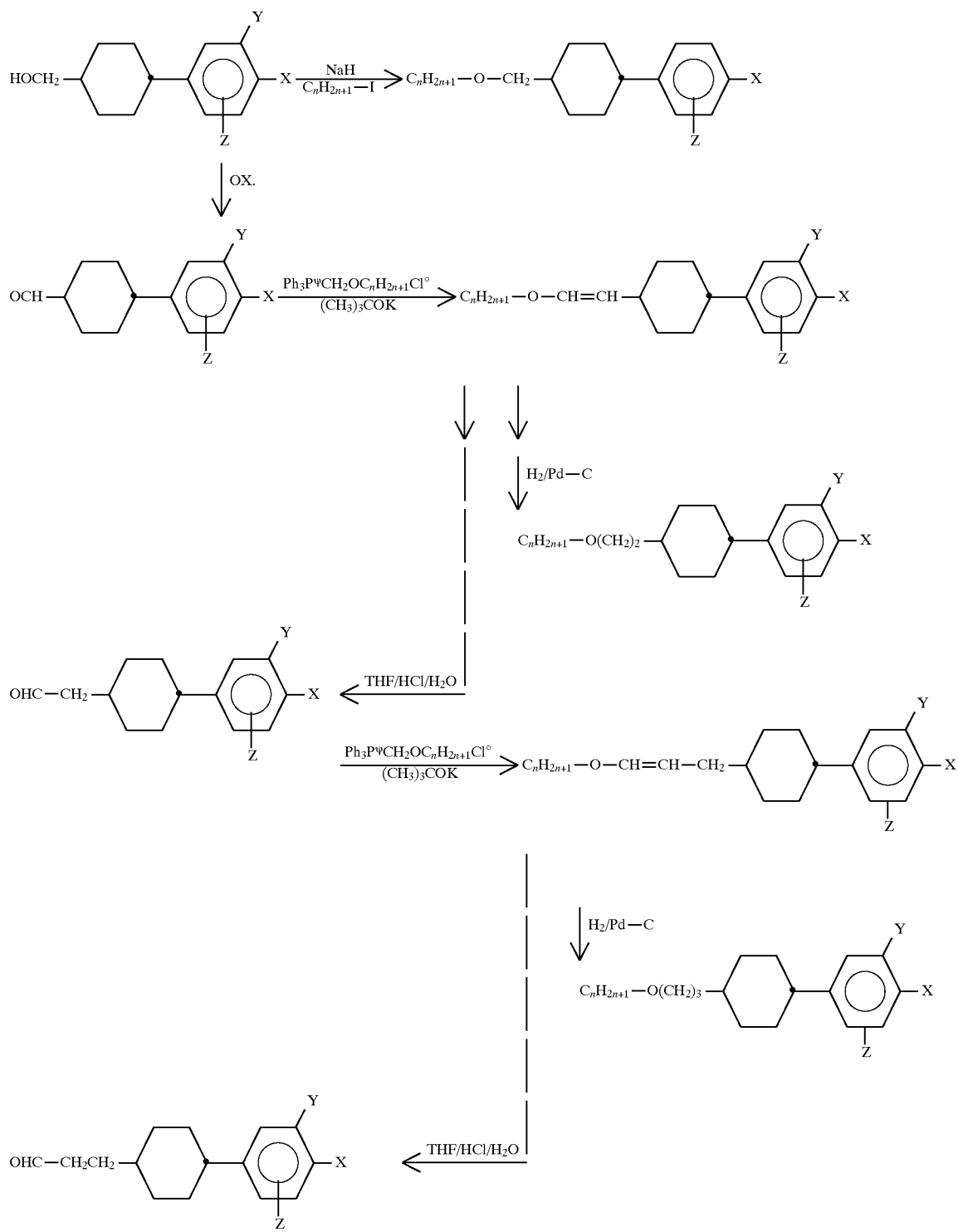

Scheme 1b

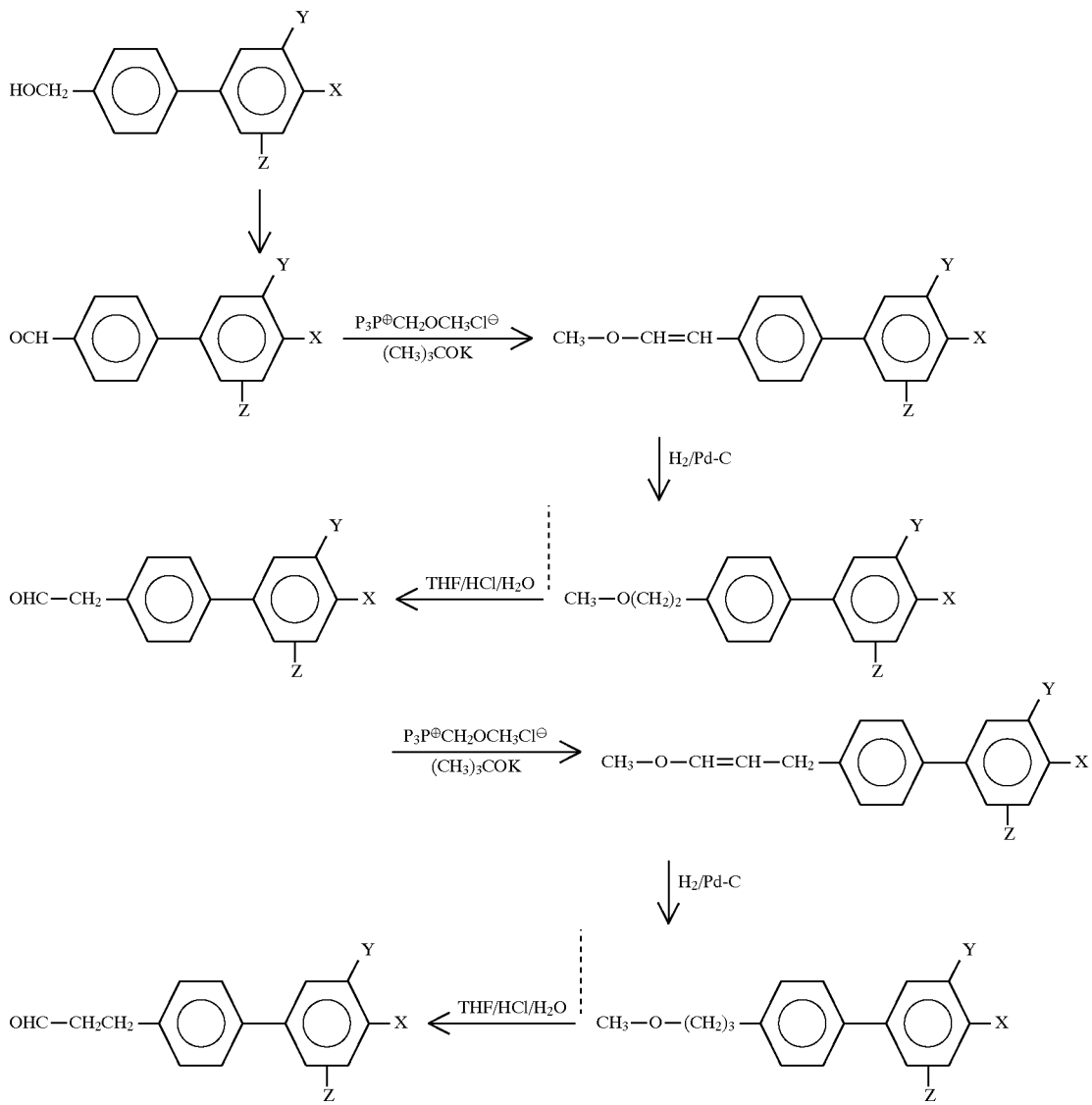

By repeating this reaction sequence analogously, the compounds where r=4 or 5 can be obtained.

The Grignard compound obtained from the corresponding bromobenzene derivative is reacted with cheorotrialkyl orthotitanate or orthozirconate in accordance with WO 87/05599 to give the tertiary cyclohexanol. Elimination of water, hydrogenation of the double bond and isomerization give the trans-cyclohexanecarboxylic acid ester by customary methods. From the latter, customary standard processes give the aldehydes which are suitable for the compounds according to the invention, which can be obtained from the former by the Wittig synthesis and subsequent hydrogenation of the double bond.

Some of the bromobenzene derivatives used as starting materials are known, and some can be obtained without difficulties from compounds known from the literature by standard methods of organic chemistry. For example, the $OCF_3$ or $OCHF_2$ compounds can be obtained by known processes from the corresponding phenols and the $CF_3$ or CN compounds can be obtained from the corresponding benzoic acids. Compounds of the formula

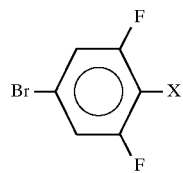

or alternatively corresponding monofluorinated compounds can be obtained, for example, from the known precursors where X=H by lithiiation at low temperatures with subsequent reaction with a suitable electrophile.

The homologization indicated in the above reaction scheme can also be carried out by other standard methods known to those skilled in the art.

The compounds according to the invention where s=2 and t=0 are synthesized in accordance with the following synthesis scheme (R=n-alkyl):

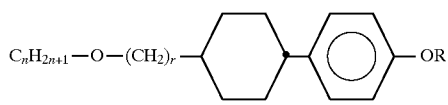
↓ POT
NMP/160°
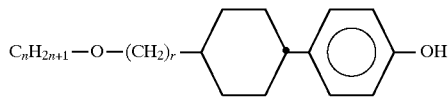
↓ 1. H₂/Pd
↓ 2. Jones oxidation
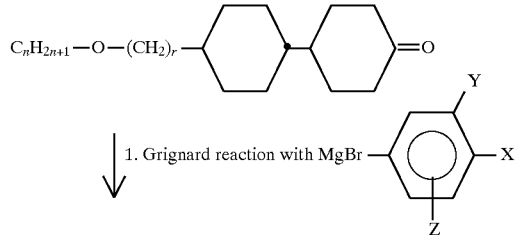
↓ 1. Grignard reaction with MgBr—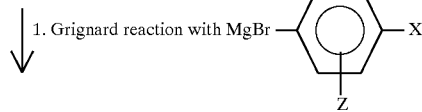
↓ 2. Elimination of water and hydrogenation
↓ 3. Isomerization
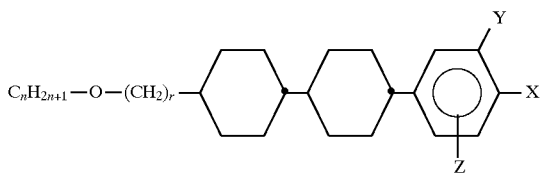
The starting materials can be obtained as follows:
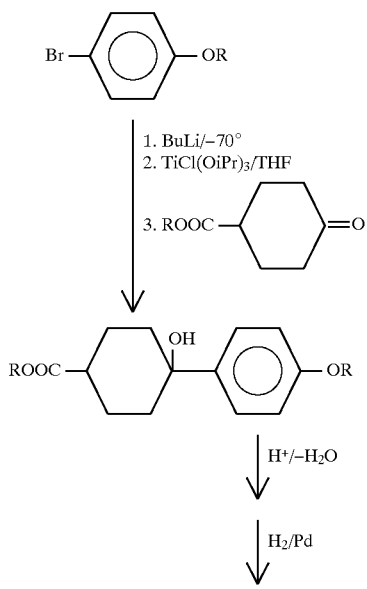

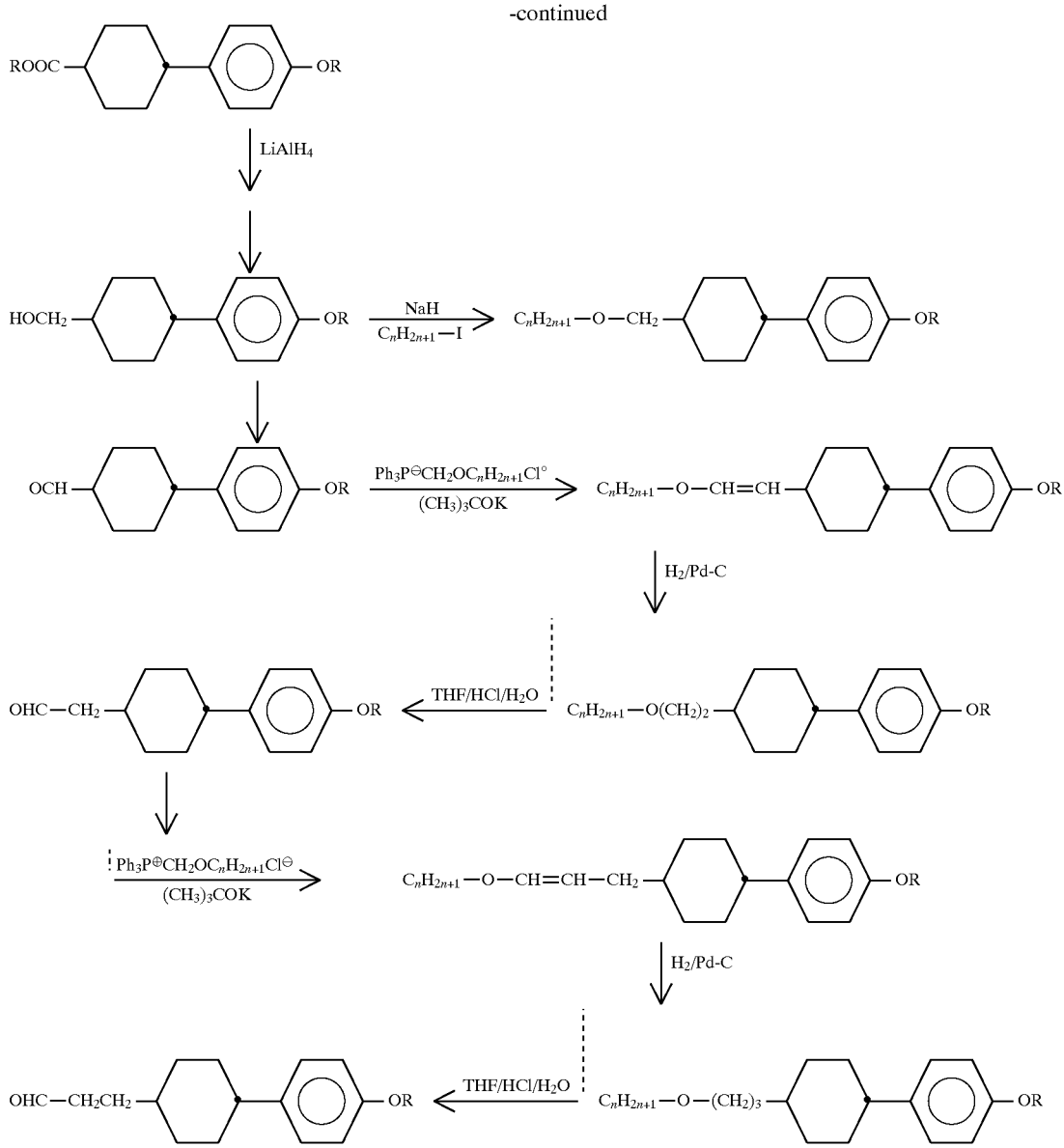
By repeating this reaction sequence analogously, the compounds where r=4 or 5 can be obtained.
A further way of preparing the preferred compounds where r=3 and n=1 is indicated below:
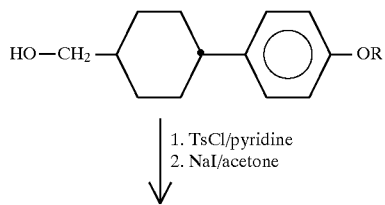
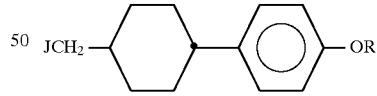
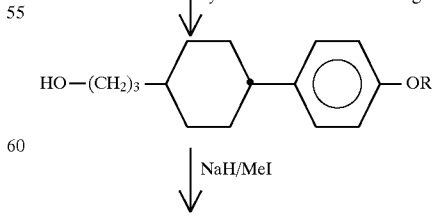

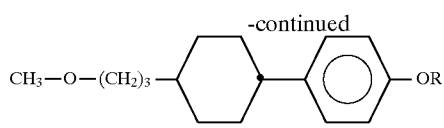
-continued

A further possible synthesis for compounds where s=2 and t=0 and a possible synthesis for compounds where s=t=1 is shown in the scheme below:

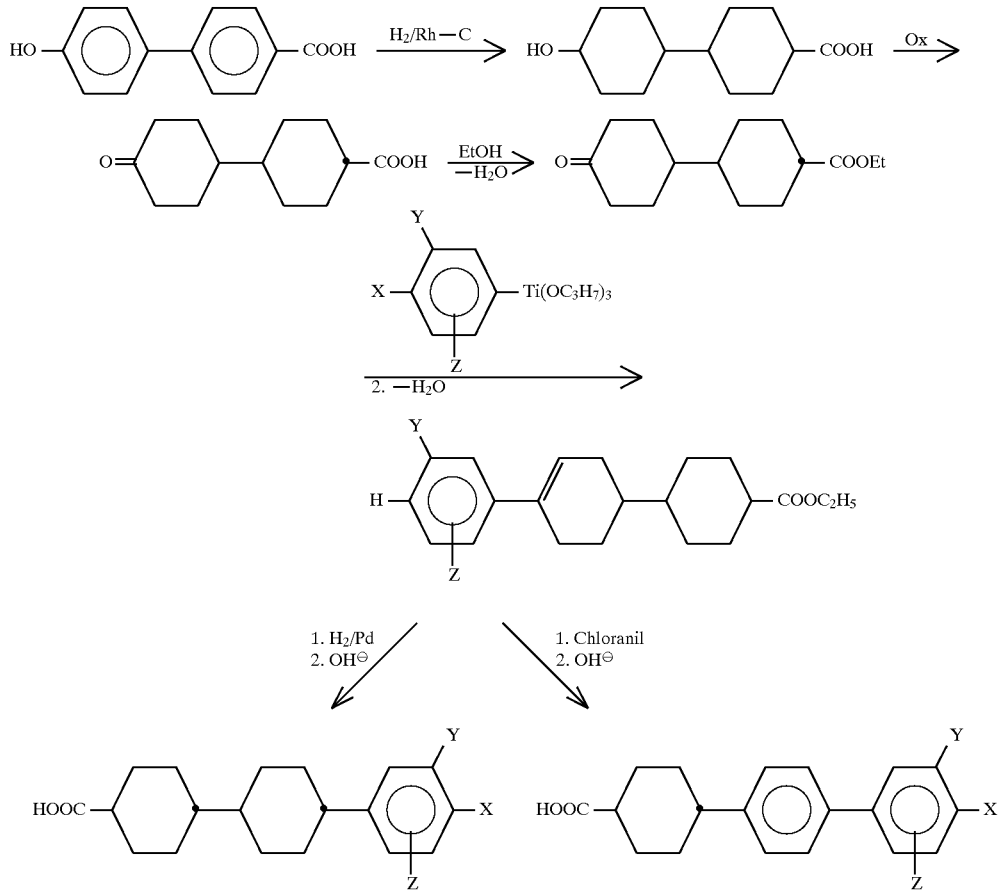

The compounds according to the invention are obtained entirely analogously to the abovementioned synthesis schemes by homologization of the cyclohexanecarboxylic acids or the corresponding aldehydes.

The compounds of the formula I where t=1 and L=F are obtained entirely analogously to the first synthesis scheme (preparation of compounds where s=1 and t=0) by using

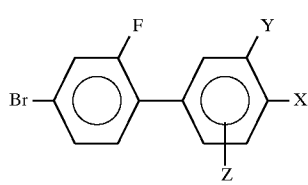

in place of the bromobenzene derivative. The bromobiphenyl compound can be prepared in a manner known per se by coupling reactions catalysed by noble metals (E. Poetsch, Kontakte (Darmstadt) 1988 (2), p. 15).

Compounds where t=1 and L=H or F may also be obtained by Pd(0)-catalysed couplings of boric acids of the formula A

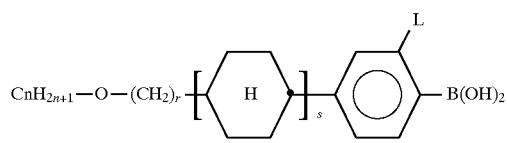

with

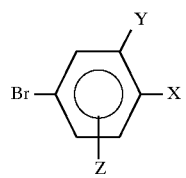

by the method of Suzuki et al.

Alternatively,

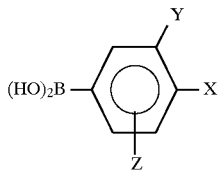

can also be coupled with appropriate halides, such as, for example, iodiodes of the formula B

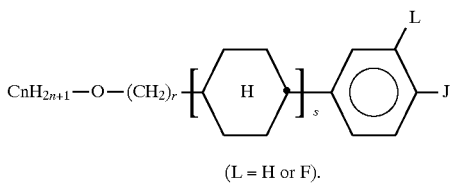

(L = H or F).

The boric acids A can be obtained from the corresponding bromides, which are themselves prepared in accordance with scheme I (X=Br, Z=H, Y=F or H).

The iodides B can be prepared analogously or the compound of the formula

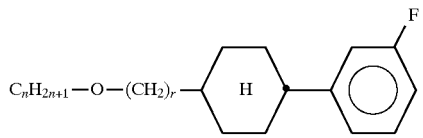

is prepared entirely analogously to scheme 1 from m-bromofluorobenzene and converted into B by orthometallation using POT/BuLi at −100° with subsequent treatment with iodine.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyriimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes and tolans.

The 1,4-phenylene groups in these compounds may also be fluorinated.

The most important compounds suitable as further constituents of media according to the invention can be characterized by the formulae 1, 2, 3, 4 and 5:

R'—L—E—R"1
R'—L—COO—E—R"2
R'—L—OOC—E—R"3
R'—L—CH₂CH₂—E—R"4
R'—L—C≡C—E—R"5

In the formulae 1, 2, 3, 4 and 5, L and E, which may be identical or different, are in each case, independently of one another, a divalent radical from the group formed by -Phe-, -Cyc-, -Phe-Phe, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe—Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compound of the sub-formulae 1b, 2b, 3b, 4b and 5b, R" is —CN, —CF₃, —OCHF₂, —OCF₃, F, Cl or —NCS; in this case, R has the meaning given for the compounds of the sub-formulae 1a to 5a and is preferably alkyl or alkenyl. R" is particularly preferably selected from the group consisting of —F, Cl, CF₃, —OCHF₂ and —OCF₃. However, other variants of the proposed substituents in the compounds of the formulae 1, 2, 3, 4 and 5 are also common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention also preferably contain components from the group comprising the compounds 1b, 2b, 3b, 4b and 5b (Group 2), whose proportions are preferably as follows:

Group 1: 20 to 90%, in particular 30 to 90%,
Group 2: 10 to 80%, in particular 10 to 50%, the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the orientation of the nematic phases.

The examples below are intended to illustrate the invention without representing a limitation. mp.=melting point, cp.=clear point. Above and below, percentages are per cent by weight; all temperatures are indicated in degrees Celsius. "Customary work-up" means that water is added, the mixture is extracted with methylene chloride, the organic phase is separated off, dried and evaporated, the product is purified by crystallization and/or chromatography.

In addition, the abbreviations have the following meanings:

C: crystalline-solid state, S: smectic phase (the index characterizes the phase type), N: nematic state, Ch: cholesteric phase, I: isotropic phase. The number between two symbols indicates the conversion temperature in degrees Celsius.

DAST Diethylaminosulfur trifluoride
DCC Dicyclohexylcarbodiimide
DDQ Dichlorodicyanobenzoquinone
DIBALH Diisobutylaluminium hydride
DMSO Dimethyl sulfoxide
POT Potassium tertiary-butanolate
THF Tetrahydrofuran
PTSOH p-Toluenesulfonic acid

EXAMPLE 1

Hydrogenation of 1-methoxy-2-[trans-4-[p-trifluoromethylphenyl)cyclohexyl]ethene [obtainable from p-bromotrifluorotoluene by the above synthesis scheme] on Pd/C and customary work-up give trans-4-methoxyethyl-(p-trifluoromethylphenyl)cyclohexane.

EXAMPLES 2 TO 61

The following compounds (Q=—(CH$_2$)$_r$—, t=0) are obtained analogously to Example 1 from the corresponding vinyl ethers:

|      | r | n | s | X      | Y | Z |
|------|---|---|---|--------|---|---|
| (2)  | 2 | 2 | 1 | —CF$_3$  | H | H |
| (3)  | 3 | 1 | 1 | —CF$_3$  | H | H |
| (4)  | 4 | 1 | 1 | —CF$_3$  | H | H |
| (5)  | 2 | 1 | 1 | F      | H | H |
| (6)  | 3 | 1 | 1 | F      | H | H |
| (7)  | 4 | 2 | 1 | F      | H | H |
| (8)  | 2 | 1 | 1 | Cl     | H | H |
| (9)  | 3 | 1 | 1 | Cl     | H | H |
| (10) | 4 | 2 | 1 | Cl     | H | H |
| (11) | 2 | 1 | 1 | —OCF$_3$ | H | H |
| (12) | 3 | 1 | 1 | —OCF$_3$ | H | H |
| (13) | 4 | 2 | 1 | —OCF$_3$ | H | H |
| (14) | 2 | 1 | 1 | —OCHF$_2$ | H | H |
| (15) | 3 | 1 | 1 | —OCHF$_2$ | H | H |

-continued

|      | r | n | s | X      | Y | Z |
|------|---|---|---|--------|---|---|
| (16) | 4 | 2 | 1 | —OCHF$_2$ | H | H |
| (17) | 2 | 1 | 1 | —CN    | F | H |
| (18) | 3 | 1 | 1 | —CN    | F | H |
| (19) | 4 | 2 | 1 | —CN    | F | H |
| (20) | 2 | 1 | 1 | —CN    | F | F* |
| (21) | 3 | 1 | 1 | —CN    | F | F* |
| (22) | 4 | 2 | 1 | —CN    | F | F* |
| (23) | 2 | 1 | 1 | F      | F | H |
| (24) | 3 | 1 | 1 | F      | F | H |
| (25) | 4 | 2 | 1 | F      | F | H |
| (26) | 2 | 1 | 1 | Cl     | F | H |
| (27) | 3 | 1 | 1 | Cl     | F | H |
| (28) | 4 | 2 | 1 | Cl     | F | H |
| (29) | 2 | 1 | 1 | CF$_3$   | F | H |
| (30) | 3 | 1 | 1 | CF$_3$   | F | H |
| (31) | 4 | 2 | 1 | CF$_3$   | F | H |
| (32) | 2 | 2 | 2 | —CF$_3$  | H | H |
| (33) | 3 | 1 | 2 | —CF$_3$  | H | H |
| (34) | 4 | 1 | 2 | —CF$_3$  | H | H |
| (35) | 2 | 1 | 2 | F      | H | H |
| (36) | 3 | 1 | 2 | F      | H | H |
| (37) | 4 | 2 | 2 | F      | H | H |
| (38) | 2 | 1 | 2 | Cl     | H | H |
| (39) | 3 | 1 | 2 | Cl     | H | H |
| (40) | 4 | 2 | 2 | Cl     | H | H |
| (41) | 2 | 1 | 2 | —OCF$_3$ | H | H |
| (42) | 3 | 1 | 2 | —OCF$_3$ | H | H, C51 S$_B$ 105 N 158,8 I |
| (43) | 4 | 2 | 2 | —OCF$_3$ | H | H |
| (44) | 2 | 1 | 2 | —OCHF$_2$ | H | H |
| (45) | 3 | 1 | 2 | —OCHF$_2$ | H | H |
| (46) | 4 | 2 | 2 | —OCHF$_2$ | H | H |
| (47) | 2 | 1 | 2 | —CN    | F | H |
| (48) | 3 | 1 | 2 | —CN    | F | H |
| (49) | 4 | 2 | 2 | —CN    | F | H |
| (50) | 2 | 1 | 2 | —CN    | F | F* |
| (51) | 3 | 1 | 2 | —CN    | F | F* |
| (52) | 4 | 2 | 2 | —CN    | F | F* |
| (53) | 2 | 1 | 2 | F      | F | H |
| (54) | 3 | 1 | 2 | F      | F | H |
| (55) | 4 | 2 | 2 | F      | F | H |
| (56) | 2 | 1 | 2 | Cl     | F | H |
| (57) | 3 | 1 | 2 | Cl     | F | H |
| (58) | 4 | 2 | 2 | Cl     | F | H |
| (59) | 2 | 1 | 2 | CF$_3$   | F | H |
| (60) | 3 | 1 | 2 | CF$_3$   | F | H |
| (61) | 4 | 2 | 2 | CF$_3$   | F | H |

*Z in the ortho position to X

EXAMPLE 62

60 ml of THF are added under an N$_2$ atmosphere to 100 mmol of NaH in the form of an oil dispersion. The mixture is mixed vigorously and heated to 45°–50° C. 120 mmol of methyl iodide are then added, and 80 mmol of trans-4-(p-trifluoromethylphenyl)cyclohexylmethyl alcohol in 20 ml of THF are subsequently added dropwise over the course of 30 minutes. The reaction mixture is then stirred for 30 minutes at the same temperature, cooled and carefully hydrolysed using aqueous THF. When the vigorous evolution of H$_2$ is complete, customary work-up gives trans-4-methoxymethyl (p-trifluoromethylphenyl)cyclohexane.

EXAMPLES 63 to 92

The following compounds (Q=—(CH$_2$)$_r$—, t=0) are obtained analogously to Example 62 from the corresponding cyclohexylmethyl alcohols:

|  | n | s | r | X | Y | Z |
|---|---|---|---|---|---|---|
| (63) | 2 | 1 | 1 | —CF$_3$ | H | H |
| (64) | 3 | 1 | 1 | —CF$_3$ | H | H |
| (65) | 4 | 1 | 1 | —CF$_3$ | H | H |
| (66) | 1 | 1 | 1 | F | H | H |
| (67) | 2 | 1 | 1 | F | H | H |
| (68) | 3 | 1 | 1 | F | H | H |
| (69) | 1 | 1 | 1 | Cl | H | H |
| (70) | 2 | 1 | 1 | Cl | H | H |
| (71) | 3 | 1 | 1 | Cl | H | H |
| (72) | 1 | 1 | 1 | —OCF$_3$ | H | H |
| (73) | 2 | 1 | 1 | —OCF$_3$ | H | H |
| (74) | 3 | 1 | 1 | —OCF$_3$ | H | H |
| (75) | 1 | 1 | 1 | —OCHF$_2$ | H | H |
| (76) | 2 | 1 | 1 | —OCHF$_2$ | H | H |
| (77) | 3 | 1 | 1 | —OCHF$_2$ | H | H |
| (78) | 1 | 1 | 1 | —CN | F | H |
| (79) | 2 | 1 | 1 | —CN | F | H |
| (80) | 3 | 1 | 1 | —CN | F | H |
| (81) | 1 | 1 | 1 | —CN | F | F* |
| (82) | 2 | 1 | 1 | —CN | F | F* |
| (83) | 3 | 1 | 1 | —CN | F | F* |
| (84) | 1 | 1 | 1 | F | F | H |
| (85) | 2 | 1 | 1 | F | F | H |
| (86) | 3 | 1 | 1 | F | F | H |
| (87) | 1 | 1 | 1 | Cl | F | H |
| (88) | 2 | 1 | 1 | Cl | F | H |
| (89) | 3 | 1 | 1 | Cl | F | H |
| (90) | 1 | 1 | 1 | CF$_3$ | F | H |
| (91) | 2 | 1 | 1 | CF$_3$ | F | H |
| (92) | 3 | 1 | 1 | CF$_3$ | F | H |

*Z in the ortho position to X

EXAMPLE 93

0.1 mol of magnesium and 0.1 mol of p-bromotrifluoromethoxybenzene are reacted under an N$_2$ atmosphere in THF to give the corresponding Grignard compound, to which is added 0.1 mol of 4-(trans-4-(4-oxapentyl)cyclohexyl)cyclohexanone, and the reaction mixture is stirred at the boil for 1 hour. The mixture is subjected to customary work-up, and the reaction product is dehydrated on a water separator by boiling with p-toluenesulfonic acid in toluene. The reaction product is subsequently hydrogenated on a Pd/C catalyst. After customary basic isomerization, the isomers are resolved by chromatography or by crystallization, to give trans,trans-4-(4-oxapentyl)-4'-(p-trifluoromethoxyphenyl)bicyclohexyl, C 51 S$_B$105 N 158.8 I.

EXAMPLE 94

A solution of 0.2 mol of p-toluenesulfonyl chloride in 75 ml of toluene is added dropwise to a solution of 0.2 mol of trans-4-(p-trifluoromethylphenyl)cyclohexylmethyl alcohol in 150 ml of pyridine with cooling at such a rate that the reaction temperature does not exceed 10° C. Stirring is continued overnight at room temperature, 250 ml of toluene are added, and the mixture is washed successively with water, 6 N HCl solution, water, 2 N NaOH solution and water. The p-toluenesulfonic acid ester is purified by crystallization after removal of the organic solvent. A solution of 0.4 mol of the resultant p-toluenesulfonic acid ester in 500 ml of toluene is added to a sodium methoxide solution obtained from 250 ml of methanol and 0.6 mol of metallic sodium. The mixture is refluxed for 3 hours and subjected to customary work-up to give trans-4-methoxymethyl(p-trifluoromethylphenyl)cyclohexane.

EXAMPLES 95 to 124

The following compounds (t=0, s=1 or 2) are obtained analogously to Example 94 from the corresponding cyclohexylmethyl alcohols:

|  | n | Q | X | Y | Z |
|---|---|---|---|---|---|
| (95) | 2 | CH$_2$ | —CF$_3$ | H | H |
| (96) | 3 | CH$_2$ | —CF$_3$ | H | H |
| (97) | 4 | CH$_2$ | —CF$_3$ | H | H |
| (98) | 1 | CH$_2$ | F | H | H |
| (99) | 2 | CH$_2$ | F | H | H |
| (100) | 3 | CH$_2$ | F | H | H |
| (101) | 1 | CH$_2$ | Cl | H | H |
| (102) | 2 | CH$_2$ | Cl | H | H |
| (103) | 3 | CH$_2$ | Cl | H | H |
| (104) | 1 | CH$_2$ | —OCF$_3$ | H | H |
| (105) | 2 | CH$_2$ | —OCF$_3$ | H | H |
| (106) | 3 | CH$_2$ | —OCF$_3$ | H | H |
| (107) | 1 | CH$_2$ | —OCHF$_2$ | H | H |
| (108) | 2 | CH$_2$ | —OCHF$_2$ | H | H |
| (109) | 3 | CH$_2$ | —OCHF$_2$ | H | H |
| (110) | 1 | CH$_2$ | —CN | F | H |
| (111) | 2 | CH$_2$ | —CN | F | H |
| (112) | 3 | CH$_2$ | —CN | F | H |
| (113) | 1 | CH$_2$ | —CN | F | F* |
| (114) | 2 | CH$_2$ | —CN | F | F* |
| (115) | 3 | CH$_2$ | —CN | F | F* |
| (116) | 1 | CH$_2$ | F | F | H |
| (117) | 2 | CH$_2$ | F | F | H |
| (118) | 3 | CH$_2$ | F | F | H |
| (119) | 1 | CH$_2$ | Cl | F | H |
| (120) | 2 | CH$_2$ | Cl | F | H |
| (121) | 3 | CH$_2$ | Cl | F | H |
| (122) | 1 | CH$_2$ | CF$_3$ | F | H |
| (123) | 2 | CH$_2$ | CF$_3$ | F | H |
| (124) | 3 | CH$_2$ | CF$_3$ | F | H |

*Z in the ortho position to X

EXAMPLES 125 to 140

The following esters according to the invention (Q=—CO—, t=0, s=1 or 2) are obtained by esterification of the corresponding trans-cyclohexanecarboxylic acids:

|  | n | X | Y | Z |
|---|---|---|---|---|
| (125) | 1 | —CF$_3$ | H | H |
| (126) | 2 | —CF$_3$ | H | H |
| (127) | 1 | F | H | H |
| (128) | 2 | F | H | H |
| (129) | 1 | Cl | H | H |
| (130) | 2 | Cl | H | H |
| (131) | 1 | —OCF$_3$ | H | H |
| (132) | 2 | —OCF$_3$ | H | H |
| (133) | 1 | —OCHF$_2$ | H | H |
| (134) | 2 | —OCHF$_2$ | H | H |
| (135) | 1 | —CN | F | H |
| (136) | 2 | —CN | F | H |
| (137) | 1 | F | F | H |
| (138) | 2 | F | F | H |
| (139) | 1 | Cl | F | H |
| (140) | 2 | Cl | F | H |

EXAMPLE 141

A solution of 0.2 mol of p-toluenesulfonyl chloride in 75 ml of toluene is added dropwise to a solution of 0.2 mol of p-(3,4-difluorophenyl)benzyl alcohol in 150 ml of pyridine with cooling at such a rate that the reaction temperature does not exceed 10° C. Stirring is continued overnight at room temperature, 250 ml of toluene are added, and the mixture is washed successively with water, 6 N HCl solution, water, 2 N NaOH solution and water. The p-toluenesulfonic acid ester is purified by crystallization after removal of the organic solvent. A solution of 0.4 mol of the resultant p-toluenesulfonic acid ester in 500 ml of toluene is added to a sodium methoxide solution obtained from 250 ml of methanol and 0.6 mol of metallic sodium. The mixture is refluxed for 3 hours and subjected to customary work-up to give 4-methoxymethyl-3',4'-difluorobiphenyl.

EXAMPLES 142 to 171

The following compounds (Q=—CH$_2$—, S=0, t=1, L=H) are obtained analogously to Example 141 from the corresponding benzyl alcohols:

|       | n | X       | Y | Z  |
|-------|---|---------|---|----|
| (142) | 2 | —CF$_3$ | H | H  |
| (143) | 3 | —CF$_3$ | H | H  |
| (144) | 4 | —CF$_3$ | H | H  |
| (145) | 1 | F       | H | H  |
| (146) | 2 | F       | H | H  |
| (147) | 3 | F       | H | H  |
| (148) | 1 | Cl      | H | H  |
| (149) | 2 | Cl      | H | H  |
| (150) | 3 | Cl      | H | H  |
| (151) | 1 | —OCF$_3$ | H | H |
| (152) | 2 | —OCF$_3$ | H | H |
| (153) | 3 | —OCF$_3$ | H | H |
| (154) | 1 | —OCHF$_2$ | H | H |
| (155) | 2 | —OCHF$_2$ | H | H |
| (156) | 3 | —OCHF$_2$ | H | H |
| (157) | 1 | —CN     | F | H  |
| (158) | 2 | —CN     | F | H  |
| (159) | 3 | —CN     | F | H  |
| (160) | 1 | —CN     | F | F* |
| (161) | 2 | —CN     | F | F* |
| (162) | 3 | —CN     | F | F* |
| (163) | 1 | CF$_3$  | H | H  |
| (164) | 2 | F       | F | H  |
| (165) | 3 | F       | F | H  |
| (166) | 1 | Cl      | F | H  |
| (167) | 2 | Cl      | F | H  |
| (168) | 3 | Cl      | F | H  |
| (169) | 1 | CF$_3$  | F | H  |
| (170) | 2 | CF$_3$  | F | H  |
| (171) | 3 | CF$_3$  | F | H  |

*Z in the ortho-position to X

EXAMPLE 172

A solution of 0.2 mol of p-toluenesulfonyl chloride in 75 ml of toluene is added dropwise to a solution of 0.2 mol of p-(3,4-difluorophenyl)phenethyl alcohol in 150 ml of pyridine with cooling at such a rate that the reaction temperature does not exceed 10° C. Stirring is continued overnight at room temperature, 250 ml of toluene are added, and the mixture is washed successively with water, 6 N HCl solution, water, 2 N NaOH solution and water. The p-toluenesulfonic acid ester is purified by crystallization after removal of the organic solvent. A solution of 0.4 mol of the resultant p-toluenesulfonic acid ester in 500 ml of toluene is added to a sodium methoxide solution obtained from 250 ml of methanol and 0.6 mol of metallic sodium. The mixture is refluxed for 3 hours and then subjected to customary work-up, to give 4-methoxyethyl-3',4'-difluorobiphenyl.

Examples are given below of media containing at least one compound of the formula I:

EXAMPLE A

A mixture comprising

7% of trans-4-methoxyethyl(p-trifluoromethylphenylphenyl)cyclohexane,

5% of p-(trans-4-butylcyclohexyl)benzonitrile,

24% of p-(trans-4-pentylcyclohexyl)fluorobenzene,

14% of p-(trans-4-heptylcyclohexyl)fluorobenzene,

15% of 2-[trans-4-(3,4-difluorophenyl)cyclohexyl]-5-butyl-1,3-dioxane,

18% of 2-[trans-4-(p-fluorophenyl)cyclohexyl]-5-ethyl-1,3-dioxane and

17% of 2-[trans-4-(p-fluorophenyl)cyclohexyl]-5-propyl-1,3-dioxane has a high electrical resistance.

EXAMPLE B

A mixture comprising

7% of trans-4-methoxymethyl-(p-trifluoromethylphenylphenyl)cyclohexane,

5% of p-(trans-4-butylcyclohexyl)benzonitrile,

24% of p-(trans-4-pentylcyclohexyl)fluorobenzene,

14% of p-(trans-4-heptylcyclohexyl)fluorobenzene,

15% of 2-[trans-4-(3,4-difluorophenyl)cyclohexyl]-5-butyl-1,3-dioxane,

18% of 2-[trans-4-(p-fluorophenyl)cyclohexyl]-5-ethyl-1,3-dioxane and

17% of 2-[trans-4-(p-fluorophenyl)cyclohexyl]-5-propyl-1,3-dioxane has a high electrical resistance.

EXAMPLE C

A mixture comprising

7% of 4-miethoxymethyl-3', 4'-difluorobiphenyl,

5% of p-(trans-4-butylcyc lohexyl )benzonitrile,

24% of p-(trans-4-pentylcyclohexyl) fluorobenzene,

14% of p-(trans-4-heptylcyclohexyl) fluorobenzene,

15% of 2-[trans-4-(3,4-difluorophenyl)cyclohexyl]-5-buty-1,3-dioxane,

18% of 2-[(trans-4-(p-fluorophenyl )cyclohexyl]-5-ethyl-1,3-dioxane and

17% of 2-[trans-4-(p-fluorophenyl)cyclohexyl]-5-propyl-1,3-dioxane has a high electrical resistance.

Further preferred compounds according to the invention are indicated below (Q=(CH$_2$)$_r$, L=Z=H, Y=F, X=Cl):

| n | r | s | t |
|---|---|---|---|
| 1 | 1 | 1 | 0 |
| 2 | 1 | 1 | 0 |
| 3 | 1 | 1 | 0 |
| 4 | 1 | 1 | 0 |
| 5 | 1 | 1 | 0 |
| 1 | 1 | 0 | 1 |
| 2 | 1 | 0 | 1 |
| 3 | 1 | 0 | 1 |
| 4 | 1 | 0 | 1 |
| 5 | 1 | 0 | 1 |
| 1 | 2 | 1 | 0 |
| 1 | 3 | 1 | 0 |
| 1 | 4 | 1 | 0 |
| 1 | 5 | 1 | 0 |

We claim:

1. A benzene compound of formula I

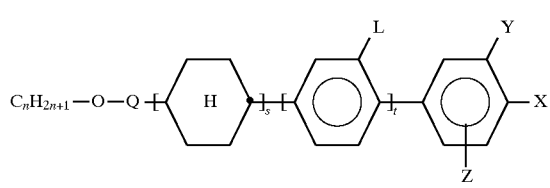

in which n is 1 to 7, Q is —CO— or —(CH$_2$)$_r$—, where r is 1 to 5, s is 1, t is 0, X is —CN, L is F, Y is F and Z is F.

2. A liquid-crystalline medium for electro-optical displays, comprising at least two liquid-crystalline components, wherein at least one component is a benzene compound of formula I according to claim 1.

3. An electro-optical display based on a liquid-crystal cell, wherein the liquid-crystal cell contains a medium according to claim 2.

4. A benzene compound of formula

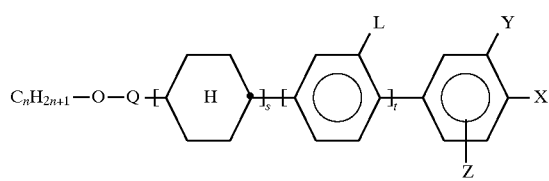

in which n is 1 to 7,
Q is —CO— or —(CH$_2$)$_r$—, where r is 1 to 5,
s is 1,
t is 0 or 1,
X is —CN,
Y is F,
Z is F, and
L is F.

* * * * *